United States Patent [19]

Sheiman et al.

[11] Patent Number: 4,791,067

[45] Date of Patent: Dec. 13, 1988

[54] AGGLUTINATION IMMUNOASSAY FOR HAPTEN INVOLVING MONOCLONAL ANTIBODY OF IGA CLASS REAGENT

[75] Inventors: Mark I. Sheiman, Nanuet; Kwok K. Yeung, Suffern, both of N.Y.; Teresa H. Chan, Wayland, Mass.

[73] Assignee: Fisher Scientific Co., Pittsburgh, Pa.

[21] Appl. No.: 66,306

[22] Filed: Jun. 25, 1987

[51] Int. Cl.⁴ .................. G01N 33/546; G01N 33/577
[52] U.S. Cl. .............................. 436/513; 435/240.27; 436/509; 436/533; 436/534; 436/548; 436/808; 436/821; 436/825; 935/103; 935/110
[58] Field of Search ............... 436/509, 533, 534, 548, 436/513, 808, 821, 825; 435/240.27; 935/103, 110

[56] References Cited

U.S. PATENT DOCUMENTS

| | | | |
|---|---|---|---|
| 4,362,531 | 12/1982 | de Steenwinkel et al. | 23/230 |
| 4,397,960 | 8/1983 | Moussebois et al. | 436/512 |
| 4,427,781 | 1/1984 | Masson et al. | 436/509 |
| 4,491,632 | 1/1985 | Wands | 435/240.27 |
| 4,582,810 | 4/1986 | Rosenstein | 436/534 X |
| 4,645,748 | 2/1987 | Hurwitz | 436/509 |
| 4,659,659 | 4/1987 | Dwek | 436/509 X |

OTHER PUBLICATIONS

M. Zrein et al., "Quantitation of Rheumatoid Factors," J. Immun. Methods, vol. 87, pp. 229–237 (1986).
L. A. Borque et al., "Immunoassay of Rheumatoid Factor by Latex Particle Counting," Clin. Chem., vol. 33, No. 5, pp. 704–707 (1987).
Opheim et al., "Particle-Enhanced Turbidimetric Inhibition Immunoassay for Theophylline Evaluated with the DuPont aca", Clin. Chem. vol. 30, No. 11, pp. 1870–74 (1984).

Primary Examiner—Sidney Marantz
Attorney, Agent, or Firm—Alan M. Doernberg

[57] ABSTRACT

An assay method and kit for a hapten such as theophylline employs a first, latex reagent and a second, antibody reagent. By using a monoclonal antibody of the IgA class in the second reagent, interference by patient rheumatoid factor is prevented.

14 Claims, No Drawings

AGGLUTINATION IMMUNOASSAY FOR HAPTEN INVOLVING MONOCLONAL ANTIBODY OF IGA CLASS REAGENT

The present invention relates to immunoassay methods and kits for detecting haptens by agglutination and especially to such methods and kits employing particle-bound hapten or hapten-analog and a second reagent comprising antibody against the hapten.

Haptens are analyte molecules which do not generally elicit an immune response, but which can be specifically bound by appropriate antibodies. One of the several types of immunoassays used to detect haptens (such as therapeutic drugs, drugs of abuse or certain hormones) is agglutination assay. In such assay, two reagents are employed: one containing the hapten, a hapten analog or a conjugate of the hapten or hapten analog with an inert protein (e.g., albumin) on a particle, the other containing antibody against the hapten. In inhibition assays the sample is first admixed with the second reagent and then the first reagent is added. In competition assays the second reagent is reacted simultaneously with first reagent and sample (which may be premixed). In either case, hapten in the sample binds to the limited sites of antibody in the second reagent so that less antibody sites are available to bind to and agglutinate the hapten-bearing particles. Agglutination is monitored visually, by absorbance, by light scatter or otherwise (e.g., by particle-counting). The reduced level of agglutination is then correlated with an increased level of hapten in the sample, commonly based upon a dose-response curve generated with controls or calibrators of known hapten concentration.

Such assays for hapten commonly employ polyclonal antibodies generated by inoculating an animal with a conjugate of the hapten (e.g., albumin-hapten conjugate). It has also been proposed to use monoclonal antibodies for such tests. The most widely available monoclonal antibodies result from mouse-mouse hybridizations and are one or another subclass of the immunoglobulin G (IgG) class. It is well known that immunoglobulins are also found of the IgA, IgE, IgM and IgD classes, which differ from each other in valency (e.g., IgG is divalent, IgM is decavalent).

Rheumatoid factor (RF) is an autoimmune antibody found in human serum which binds to the Fc fragment of IgG antibodies. RF is normally present at low levels, but can be present at elevated levels under various conditions and disease states. For some individuals, e.g., those with rheumatic arthritis, the RF concentration varies over time. In some diagnostic immunoassays the sample is pre-treated (e.g., with 2-mercaptoethanol or dithiothreitol) to inactivate RF activity prior to or during the assay. Otherwise, RF may interfere with the assay, especially by promoting agglutination even where analyte hapten has blocked many of the reagent antibody sites. If, for example, many of the divalent reagent antibodies have bound one sample hapten molecule, they can still bind at the other site to particle-bound hapten. With such monovalent binding, however, no agglutination would result; but the Fc fragment of the reagent antibody would be exposed on the particle. Elevated sample RF could agglutinate the particles via such Fc fragments. A somewhat analogous use of reagent RF as an agglutinator in particle assays for hapten is described in U.S. Pat. No. 4,427,781 to Masson (1984).

U.S. Pat. No. 4,397,960 to Moussebois, et al (1983) describes the use of F(ab')$_2$ fragments of antibodies against antigens, free of the Fc fragment, in immunoassays. It is indicated that the use of such F(ab')$_2$ fragments as particle-bound antibodies reduces the interference by endogenous RF (which would agglutinate such particles even in the absence of analyte antigen). See also U.S. Pat. No. 4,362,531 to de Steenwinkel, et al (1982) and EPA No. 83,869 on reducing other interferences by the use of chaotropic agents and the use of nonhomologous F(ab')$_2$ fragments.

BRIEF DESCRIPTION OF THE INVENTION

The present invention provides for the use of monoclonal antibodies of the IgA class in inhibition and competition agglutination immunoassays for hapten. Thus, the present invention provides a method for detecting a hapten in a serum, plasma or blood sample which comprises the steps:
(a) admixing the sample with:
 (1) a first reagent comprising particles bearing the hapten or an analog of the hapten suspended in an aqueous medium, and
 (2) a second reagent comprising an antibody against the hapten in an amount and of an activity sufficient to agglutinate the particles in the absence of hapten in the sample, but to cause reduced amounts of agglutination with increasing amounts of hapten in the sample; and
(b) detecting the degree of agglutination as a measure of the presence and amount of hapten in the sample as characterized by the antibody in the second reagent being a monoclonal antibody of the IgA class, whereby interference by rheumatoid factor or Clq in the sample is eliminated.

The present invention further provides a kit for detecting a hapten in a serum, plasma or blood sample which comprises:
(a) a first reagent comprising particles bearing the hapten or an analog of the hapten suspended in an aqueous medium, and
(b) a second reagent comprising a monoclonal antibody against the hapten of the IgA class of activity capable of agglutinating the particles of the first reagent.

A corresponding method and kit can also be used to detect or determine antigens. In such case, the antigen or an analog of the antigen would be used in the first reagent and an antibody against the antigen (e.g., monoclonal beta-hCG of class IgA) would be used in the second reagent to detect the antigen (e.g., beta-human chorionic gonadotropin).

DETAILED DESCRIPTION OF THE INVENTION

The first reagent used in the present invention contains particles bearing the hapten to be analyzed or an analog of that hapten which would be bound by the same antibody (e.g., oubain as an analog of digoxin). The hapten can be a therapeutic drug such as gentamicin, digoxin, theophylline, phenobarbitol, phenytoin, amikacin, tobramycin, carbamazepine, primidone, quinidine, procainamide or valproic acid. The hapten can also be a drug of abuse such as cocaine, tetrahydrocannabinol, morphine, heroin. amphetamine or methadone. The hapten can also be a hormone or other small biological molecule such as thyroxine or cortisol. The hapten can also be an antibiotic or fragment thereof such as penicillin (or the cepham nucleus thereof).

When the kit and method are used to detect an antigen, any of the various antigens commonly detected (including hormones, viral antigens bacterial antigens) can be used in the first reagent, with the corresponding monoclonal antibody used in the second reagent.

In the following description, theophylline will be referred to as an exemplary hapten in describing the hapten conjugate, the particle-bound hapten and the anti-hapten antibody. It should be understood that any of a variety of haptens can be similarly detected by appropriate substitution of that hapten (and its antibody) for theophylline (and anti-theophylline monoclonal antibody) or (for antigens) by the appropriate substitution of antigen (and its antibody).

While the hapten itself can be coated onto particles, it is preferred to first prepare a conjugate of the hapten with an inert protein, e.g., albumin. Such conjugates are themselves well known and are, in fact used to elicit an immune response so as to generate the desired antibody. Albumin from various sources can be used and is widely available: e.g., bovine serum albumin (BSA), human serum albumin (HSA) or corresponding materials from various sources such as chicken, rabbit, mouse, goat or pig. HSA is preferred. The hapten can be chemically attached to the protein at a variety of reactive sites (e.g., the free amine sites in HSA). Commonly, a derivative of the hapten (e.g., theophylline butyric acid or TBA) is used to introduce a spacer between the protein and the hapten.

The number of hapten molecules derivatives or analogs per protein molecule is not independently critical, since compensation can be made in either the number of conjugate molecules per particle or the ratio or particles to antibody. Nevertheless, it is preferred to place multiple haptens on each protein molecule without saturation of the active (e.g., amine) sites in the protein; it is especially important to have such sites available if they are to be used subsequently to link the conjugate to the particle. If activation is to be used in linking hapten to protein, it is preferred to activate the hapten rather than the protein. In the case of TBA conjugated with HSA, a molar ratio of 2.5:1 to 5.0:1 of TBA:HSA is preferred, since sufficient amine groups remain for further reaction.

The conjugate (or less preferably hapten alone) can be attached to particles by simple adsorption, by covalent attachment or by specific hydrogen bonding or other non-covalent attachment (e.g., particle-bound avidin attaching biotin-hapten conjugate). Preferably the hapten-protein conjugates are attached to particles covalently. While various biological particles (e.g., cells), inorganic particles (e.g., bentonite, metal sols), and other organic particles (e.g., liposomes) can be used, polymeric particles of generally uniform size are preferred. Exemplary are polystyrene latex particles and especially derivatized polystyrene latex particles having amine, carboxyl or other reactive functionality. In the exemplary case, residual amine functionality of TBA-HSA conjugates can be attached to carboxyl functionality of carboxy latex beads by conventional carbodiimide chemistry.

The size of the particles is not independently critical, and may be a function of the eventual visual or spectrophotometric read-out to be used to determine the degree of agglutination. To increase speed of the immunochemical reaction, relatively small particles (e.g., polymeric particles of about 0.02 to about 0.2 micrometer diameter) are preferred, although somewhat larger particles (up to 1.0 micrometer diameter) in many cases can be used and very large particles e.g., 5 or 10 micrometers in diameter for cells) can be used, but are not preferred. The preferred small particles are exemplified by 0.09 micrometer diameter carboxy latex particles.

The amount of hapten (or preferably conjugate) per particle is also not independently critical, but can be compensated, e.g., by the hapten/protein ratio, the particle concentration in the first reagent or the antibody concentration in the second reagent. Once a conjugate is prepared, it may be desirable to determine optimal conjugate/particle ratios empirically. Normally, however, a recipe is established for a fixed ratio quantity of a particular conjugate to particles and also to various diluents activators such as carbodiimides and other coreactants). Typically, the particles are first washed and then assayed and then activated and then reacted with conjugate and then inactivated and then diluted and then sonicated (to break up clumps) and then washed (with centrifugation between each wash step and sonication during each wash step). Finally the latex-conjugate can be diluted in the desired suspension medium to the desired concentration (frequently expressed as an optical density at a particular wavelength) that is empirically established. Changes in such concentration can be compensated by adding diluent later to the reaction mixture: separately, with the sample or with the second (antibody) reagent.

The second reagent contains a monoclonal antibody which is not of the immunoglobulin G class (IgG) but is normally of the immunoglobulin A class (IgA). Antibodies of other classes (IgE, IgD or IgM) would be suitable if and only if they shared the important properties of IgA monoclonal antibodies; agglutination of hapten conjugate in particles in the absence of dissolved hapten which is inhibited progressively by dissolved hapten and insensitivity of such reaction to RF even in reasonably high levels (e.g., an RF titer of 800 Iu/ml). The monoclonal antibody can be the result of hybridizing mouse B-cells with mouse myelomas (mouse-mouse hybridomas) or other hybridization of antibody-producing cells with immortal cells. The selection of cell lines producing antibodies of the desired specificity e.g.. antitheophylline) and type (e.g., IgA) can proceed by conventional techniques. Similarly, the recovery and purification of the antibody to pure or semi-pure form can follow conventional techniques. Furthermore, many such monoclonal antibodies are commercially available, with the immunoglobin class being designated by the supplier or readily ascertainable by convention techniques (e.g., mouse ascites fluid containing anti-theophylline identified by the supplier as from clone 5BC1-BE3 and as being of class IgA).

In the second reagent, the monoclonal antibody is normally combined with various constituents such as pH buffers, proteins (e.g., bovine gamma globulin), salts and preservatives (e.g., sodium azide). For use in conjunction with a particular lot of first reagent, either the concentration of the first or second reagents can be diluted to a level that empirically gives a good dose-response curve on the instrument (or visibility technique) to be used to assay patient samples.

The assay, and thus also the procedures with calibrators of known hapten concentration used to establish certain dilution ratios, can be established in either an inhibition mode or a competition mode. In the inhibition mode. the sample is incubated with second reagent so as to permit most or all of the hapten in the sample to bind to antibody in second reagent. Such reactions are usually assayed within one to four minutes at either 30° C. or 37° C. provided that adequate mixing has occurred. In two-compartment cuvettes, such as are found in multicuvette rotors of centrifugal analyzers, the sample and second reagent would be loaded together into one compartment (typically the inner compartment). The first reagent would then be admixed with the incubation product e.g., by accelerating the rotor so that sample and second reagent overflows a dam and mixes with first reagent in each outer compartment. By taking one or more measurements immediately after mixing and another after sufficient time for agglutination of particles by antibody to be complete, a difference can be measured which can be correlated with hapten concentration in a fixed quantity of sample.

In similar fashion a competition assay can be set up by reacting the antibody in the second reagent simultaneously with hapten in the sample and hapten on the particles in the first reagent. While all three constituents can be combined simultaneously for convenience, one would normally admix sample with first reagent (no reaction will occur), e.g., in the inner compartment of a cuvette of a rotor, and then mix that mixture with second reagent e.g., in the outer compartment of the same cuvette.

The agglutination can be monitored visually or, preferably, spectrophotometrically in an absorbance or light scatter mode. Depending upon the particle size and wavelength, agglutination will cause either an increase or decrease in absorbance. For example, using 0.09 micrometer diameter particles monitored at 340 nm agglutination leads to an increase in absorbance (unagglutinated particles are smaller than the wavelength of the light by a factor of almost 4). Instead of measuring a difference between initial and final values, or can also monitor absorbance (or light scatter or nephelometry or fluorescence) over the course of the reaction and determine a slope (or proceed with some form of curve fitting analysis).

EXAMPLES

Example 1

Assay For Theophylline Employing IgA Monoclonal Antibody

A. Preparation of Conjugate

For each liter of latex reagent to be prepared, 15 mg of theophylline butyric acid (TBA), 9.0 mg of dicyclohexyl-carbodiimide (DCC), 6.0 mg of N-hydroxy succinimide (HOSu) and 0.7 ml N, N-dimethylformamide (DMF) were used. The TBA, DCC and HOSu were weighed into a glass test tube, the DMF added (in a fume hood) and the contents vortexed to dissolve all components. The tube was wrapped in aluminum foil and left at room temperature 24–28 hours. The reaction mixture was then filtered to remove the acylurea crystals and the filtrate was used the same day.

To the above, 260 mg of human serum albumin, 13.1 ml of water 1.6 ml of pyridine and 0.56 ml of activated TBA were then added. Initially, 300 mg of HSA were mixed with 7.5 ml water in a clean glass beaker. This solution was then filtered through a 0.2 micron filter and the protein concentration determined via its absorbance at 280 nm (after dilution). Based on this assay, further water and HSA were added to achieve the desired amounts. In a fume hood, the HSA, water and then pyridine were added to a screw cap glass container and mixed gently until homogeneous; then the activated TBA was added. Mixing continued until the container was placed on a reciprocating or rotating mixer, where reaction was continued for 16–24 hours at room temperature. The reaction product was then dialyzed against 0.025 molar sodium bicarbonate over three to four days with repeated changes of dialysis buffer. The dialysate was then filtered through a 0.2 micron filter and protein concentration was determined via the Pierce BCA Protein Assay at 550 nm the assay is a dye-binding assay based upon protein reacting with alkaline copper II to produce copper I, which reacts with reagent dye as measured at 550 nm). The product solution was also measured for absorbance at 280 nm, which measures both HSA and theophylline absorbance. From these measurements versus measurement of HSA of known concentration, the molar concentrations of HSA/ml and of theophylline/ml were determined and the molar ratio of theophylline to HSA determined. If that ratio was 2.5 to 4.0, the conjugate was deemed acceptable. The theophylline-HSA conjugate was then stored at 2°–6° C. and was then used within one week.

Preparation of Latex Reagent

For each liter of final latex suspension, 175 mg of Theo-HSA conjugate, 525 mg washed latex (carboxypolystyrene of 0.09 micron diameter) and 350 mg of 1-ethyl-3-(3-dimethylaminopropyl) carbodiimide (EDCI) were used.

The latex was washed repeatedly with sterile filtered deionized water (sonicating during wash and centrifuging between washes) and its concentration monitored by absorbance at 340 nm. Sodium bicarbonate, 0.025 M, was used as diluent in an amount causing latex plus conjugate plus diluent to be 36.75 ml total volume per liter of final products. The latex and diluent were placed in a screw cap container and mixed with a magnetic stir bar to evenly disperse the components. EDCI was then dissolved in water and the solution poured evenly and down the side of the screw cap container. The mixture was then incubated 16–24 hours at room temperature. Glycine (1M pH 8.0, 5.25 ml per final liter) was then added, followed by incubation for 2 hours. Dilution was then made with 58 ml per final liter of latex wash buffer (7.51 g/l glycine, 9.93 g/l NaCl, 1.0 g/l sodium azide, 10 g/l HSA, 1.0 ml/l Triton X-100 in deionized water, adjusted to a pH of 9.0 and sterile filtered). Aliquots of the reaction mixture were then washed repeatedly in the same latex wash buffer by adding buffer to the pellet, sonicating and vortexing, adding more buffer, centrifuging, and aspirating the supernatant to form the next pellet. After repeated washing, the latex was resuspended in latex diluent (3.72 g/l EDTA, 11.25 g/l glycine, 29.22 g/l NaCl, 1.0 g/l sodium azide, 3.5 g/l GAFAC and 10 g/l HSA, ajusted to pH 9.0 and sterile filtered). The optical density was then measured, and further latex diluent was then added to achieve an optical density of 1.15 to 1.25 (340 nm).

Antibody Reagent

An antibody diluent reagent containing 3.72 g/l EDTA 1.42 g/l Na$_2$HPO$_4$, 8.77 g/l NaCl, 1.0 ml/l Durotex, 1.0 g/l sodium azide, 15 g/l bovine gamma globulin (BGG) was prepared by adding all ingredient except BGG to deionized water (approximately 70% of final volume), adjusting the pH to 7.4, adding BGG and adding the remaining deionized water. This reagent was sterile filtered before use. Theophylline monoclonal antibody from Clone 58C1-BE3 of the class IgA was then diluted with this diluent to an empirically derived amount (typically 0.2 mg/ml).

Assay

Reactions were then set up using the above latex reagent (O.D. 1.15 to 1.25 at 340 nm) and above antibody reagent by loading the inner well of each of six cuvettes with 2 ul of "sample" (a calibrator with known amounts of theophylline), 10 ul of sample diluent (water) and 50 ul of second reagent. Also loaded into the outer well of each of the cuvettes was a total of 180 ul of reagent diluent and first reagent. The theophylline concentrations for each of six calibrators (called Cal A through Cal F, respectively). are 0, 2.5, 5.0, 10.0, 20.0 and 40.0 ug/ml. That dilution of reagents was chosen which yielded a desired linearity of measurements using criteria such as:
  a delta for Cal A (0.0) at least 0.30 absorbance units,
  a delta for Cal F (40.0) no more than 0.05 absorbance units,
  differences between deltas for Cal A and Cal B of at least 0.06 absorbance units and between Cal E and Cal F of at least 0.035 absorbance units.

For acceptance, values for three levels of a serum control (Therachem Plus) had to be within printed ranges.

Results

The following are representative values obtained using Antibody Reagent Lot 143-037 and Latex Reagent Lot 144-037:

| | |
|---|---|
| Delta Absorbance (Cal A) | 0.397 |
| Delta Absorbance (Cal F) | 0.038 |
| Delta Absorbance (Cal E-Cal F) | 0.046 |
| Delta Absorbance (Cal A-Cal B) | 0.107 |

Three levels of Therachem Plus controls (from Fisher Scientific Company) were then tested. The results of ten replications of each level were:

| | |
|---|---|
| Level 1 (control lot 436-066) | 5.2 ug/ml |
| Level 2 (control lot 437-066) | 14.2 ug/ml |
| Level 3 (control lot 438-066) | 29.4 ug/ml | which were within printed ranges for each control.

Example 2

Comparison of Rabbit Polyclonal Antibody to IgA Monoclonal Antibody

Rabbit polyclonal antibody was compared to IgA monoclonal antibody by performing the theophylline assay under the same conditions as in Example 1 except that rabbit polyclonal antibody was diluted to approximately 1.0 mg/ml (instead of monoclonal IgA antibody to approximately 0.2 mg/ml) in the antibody diluent. Both tests were run on Therachem Plus control level III alone, three parts of such control mixed with one part of a patient sample pool containing an RF titer of 1500 Iu/ml and one part of such control mixed with one part of the high RF patient sample pool. The results (in ug/ml) were:

| | Rabbit Polyclonal Antibody | | | IgA Monoclonal Antibody | | |
|---|---|---|---|---|---|---|
| | Observed | Expected | % Recovery | Observed | Expected | % Recovery |
| Control Level III | 26.0 | — | — | 27.3 | — | — |
| RF + Control (1:4) | 8.2 | 19.5 | 42% | 20.3 | 20.5 | 99 |
| RF + Control (1:2) | 1.2 | 13.0 | 9% | 15.7 | 13.7 | 115 |

These results indicate that the recovery of theophylline from the high rheumatoid factor samples was significantly lower when polyclonal antibody was used than when IgA monoclonal antibody was used.

Example 3

Evaluation of Monoclonal IgG Antibody

Example 1 was repeated except that a monoclonal antibody of class IgG was diluted 1:50 (to about 0.4 mg/ml) and 1:100 (to about 0.2 mg/ml) with the antibody diluent reagent and used as second reagent. There was no significant agglutination when either dilution of antibody was used with the latex reagent and, accordingly no dose-response curve could be generated.

What is claimed is:

1. A method for detecting a hapten in a serum plasma or blood sample which comprises the steps:
  (a) Admixing the sample with:
    (1) a first reagent comprising particles bearing the hapten or an analog of the hapten suspended in an aqueous medium, and
    (2) a second reagent comprising an antibody against the hapten in an amount and of an activity sufficient to agglutinate the particles in the absence of hapten in the sample but to cause reduced amounts of agglutination with increasing amounts of hapten in the sample; and
  (b) detecting the degree of agglutination as a measure of the presence and amount of hapten in the sample; characterized by the antibody in the second reagent being a monoclonal antibody of the IgA class, whereby interference by rheumatoid factor or Clq in the sample is eliminated.

2. The method of claim 1 wherein the monoclonal antibody of the IgA class is produced from a mouse-mouse hybridoma.

3. The method of claim 1 wherein the particles in the first reagent are polymeric particles of about 0.02 to about 0.2 micrometer diameter.

4. The method of claim 1 wherein the particles bear a conjugate of the hapten with an inert protein.

5. The method of claim 4 wherein the inert protein is albumin.

6. The method of claim 1 wherein the sample is first admixed with second reagent and then the reaction product is admixed with the first reagent, whereby the method is an inhibition assay.

7. The method of claim 6 wherein the sample and second reagent are each introduced into a first compartment of a cuvette of a rotor, the first reagent is introduced into a second compartment of the cuvette of the rotor and the rotor is then spun to cause the material in the inner compartment of the cuvette to overflow a dam into the outer compartment of the cuvette so as to admix the reaction product with the first reagent.

8. The method of claim 7 wherein the degree of agglutination is detected by measuring the absorbance of light passing through the outer cuvette of the rotor.

9. The method of claim 1 wherein the second reagent is mixed simultaneously with sample and with first reagent.

10. A kit for detecting a hapten in a serum plasma or blood sample which comprises:
(a) A first reagent comprising particles bearing the hapten or an analog of the hapten suspended in an aqueous medium and
(b) A second reagent comprising a monoclonal antibody against the hapten of the IgA class of activity capable of agglutinating the particles of the first reagent.

11. The kit of claim 10 wherein the mono clonal antibody of the IgA class is produced from a mouse-mouse hybridoma.

12. The kit of claim 10 wherein the particles in the first reagent are polymeric particles of about 0.02 to about 0.2 micrometer diameter.

13. The kit of claim 10 wherein the particles bear a conjugate of the hapten with an inert protein.

14. The kit of claim 13 wherein the inert protein is albumin.

* * * * *